United States Patent
Levy et al.

(10) Patent No.: US 6,642,433 B1
(45) Date of Patent: Nov. 4, 2003

(54) FGL-2 KNOCKOUT MICE

(75) Inventors: Gary Levy, Thornhill (CA); Philip Marsden, Toronto (CA); Laisum Fung, Toronto (CA)

(73) Assignee: Trillium Therapeutics Inc., Toronto (CA)

( * ) Notice: Subject to any disclaimer, the term of this patent is extended or adjusted under 35 U.S.C. 154(b) by 0 days.

(21) Appl. No.: 09/689,872

(22) Filed: Oct. 13, 2000

Related U.S. Application Data (63) Continuation-in-part of application No. 09/442,143, filed on Nov. 15, 1999, now Pat. No. 6,403,089, which is a continuation-in-part of application No. PCT/CA98/00475, filed on May 15, 1998.

(60) Provisional application No. 60/061,684, filed on Oct. 10, 1997, and provisional application No. 60/046,537, filed on May 15, 1997.

(51) Int. Cl.[7] .................. A01K 67/027; A01K 67/00; C12N 15/00; C12N 15/63; C12N 15/87

(52) U.S. Cl. ................ 800/18; 800/21; 800/22; 800/13; 800/14; 435/455; 435/463; 435/325

(58) Field of Search ................ 435/455, 463, 435/320.1, 325; 800/3, 18, 21, 22, 25, 13, 14

(56) References Cited

U.S. PATENT DOCUMENTS

| | | | |
|---|---|---|---|
| 5,554,593 A | 9/1996 | Nakaya et al. | 514/12 |
| 5,589,363 A | 12/1996 | Roy et al. | 435/69.6 |

FOREIGN PATENT DOCUMENTS

| | | |
|---|---|---|
| EP | 0278776 | 8/1988 |
| WO | WO 93/02705 | 2/1993 |

OTHER PUBLICATIONS

Moreadith et.al.; Gene targeting in embryonic stem cells: the new physiology and metabolism, 1997, J Mol Med 75: 208–216.*
Mullins et.al.; Perspective Series: Molecular Medicine in Genetically Engineered Animals, 1996, J. Clin. Invest. vol. 97, No. 7L 1557–1560.*
Parr et.al.; Association of Mouse Fibrinogen–Like Protein with Murine Hepatitis Virus–Induced Prothombinase Activity, 1995, Journal of Virology : 5033–5038.*
Short, cDNA Cloning: Lambda Vectors, 1998, Nucleic Acids 16: 7583–7600.*
Capecchi; Targeted Gene Replacement, 1994, Scientific American: vol. 270: 34–41.*
Wall; Transgenic Livestock: Progress and Prospects For The Future, 1996, Theriogenology 45: 57–68.*
Fingerote et al., J. of Virology, vol. 70, No. 7, p. 4275–4282, XP002077564 (1996).
Pope et al., J. of Immunology, vol. 156, p. 3342–3349, XP002077565 (1996).
Rü egg and Pytela, Gene, vol. 160, p. 257–262, XP002077567 (1995).
Koyama et al., Proc. Natl. Acad. Sci. USA, vol. 84, p. 1609–1613, XP002077568 (1987).
Van Regenmortel, M.H.W., Methods: A Companion to Methods of Enzymology, 9:465–472, 1996.

* cited by examiner

Primary Examiner—Deborah Crouch
Assistant Examiner—Thai-An N. Ton
(74) Attorney, Agent, or Firm—Bereskin & Parr; Micheline Gravelle

(57) ABSTRACT

A knockout mouse in which the Fgl-2 gene has been suppressed is described. The mouse is useful in studying the role of Fgl-2 in normal and disease states including viral hepatitis, allograph rejection, fetal loss, inflammatory bowel disease, lupus glomerulonephritis; acute respiratory disease syndrome, Whipple's disease, cancer and for developing therapies to treat these diseases.

12 Claims, 11 Drawing Sheets

Probe: lacZ (NLS)

WT: No lacZ copy

-/- homozygote: 2 copies

+/- heterozygote: 1 copy only

Primers for WT: fgl2KO-1 and fgl2 KO-2 Amplicon: 373 bp

Primers for targeted: fgl2KO-1 and lacZ (NLS) Amplicon: 319 bp

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: mfgl2-KO1 primer

<400> SEQUENCE: 1
tgctcaaaga agtgcggacc ct                    22

<210> SEQ ID NO 2
<211> LENGTH: 21
<212> TYPE: DNA
<213> ORGANISM: Artificial Sequence
<220> FEATURE:
<223> OTHER INFORMATION: mfgl2-KO2 primer

<400> SEQUENCE: 2
cacctacccg gctgtgactg c                     21

<210> SEQ ID NO 3
<211> LENGTH: 19
<212> TYPE: DNA
<213> ORGANISM: Artificial Sequence -continued

```
<220> FEATURE:
<223> OTHER INFORMATION: lacZ-AS in NLS primer

<400> SEQUENCE: 3
cccatgctcc ccactttgc                                               19

<210> SEQ ID NO 4
<211> LENGTH: 21
<212> TYPE: DNA
<213> ORGANISM: Artificial Sequence
<220> FEATURE:
<223> OTHER INFORMATION: mfgl2-KO4 primer

<400> SEQUENCE: 4
gccccactgc ttctccttcc t                                            21
```

FGL-2 KNOCKOUT MICE

The present application is a continuation-in-part of U.S. application Ser. No. 09/442,143, filed on Nov. 15, 1999 now U.S. Pat. No. 6,403,089, which is a continuation of PCT/CA98/00475, filed on May 15, 1998, which claims the benefit of U.S. provisional patent application No. 60/061,684, filed on Oct. 10, 1997 and U.S. provisional patent application No. 60/046,537, filed on May 15, 1997, all of which are incorporated herein by reference in their entirety.

FIELD OF THE INVENTION

The present invention relates to mammals and cell lines in which the expression of the Fgl-2 gene has been suppressed. The invention also includes constructs that are useful in preparing the mammals and cell lines.

BACKGROUND OF THE INVENTION

Fulminant viral hepatitis is characterized by the rapid appearance of jaundice, coagulopathy and encephalopathy and reflects severe hepatocellular dysfunction and necrosis. Thrombosis is a common feature of fulminant hepatitis and may occur in viral infections complicated by disseminated intravascular coagulation. Monocytes/macrophages respond to infection with hepatitis viruses by generating procoagulant activity (PCA) and also produce monokines such as TNF and IL-2, which in turn can induce other cells like endothelial cells to produce PCA. Activation of the coagulation pathways is an important part of immune and inflammatory reactions and accounts for the fibrin deposition in these reactions. Furthermore, the inventors have shown that the elaboration of PCA by monocytes/macrophages parallels the susceptibility to fulminant hepatitis caused by murine hepatitis virus strain 3 (MHV-3). As described in applicant's co-pending application Ser. No. 09/442,143, which is incorporated herein by reference in its entirety, the applicant's identified the MHV-3 induced procoagulant as a direct prothrombinase Fgl-2 and the mouse and human sequences have been sequenced. Clinical conditions other than hepatitis in which Fgl-2 is implicated include allograft rejection, fetal loss, inflammatory bowel disease lupus glomerulonephritis, acute respiratory disease syndrome, Whipple's disease, and cancer.

In view of the role of Fgl-2 in various diseases it is useful to prepare an Fgl-2 knockout model in order to further elucidate its function in these diseases and importantly to develop therapies to treat the diseases.

SUMMARY OF THE INVENTION

The present inventors have prepared vectors comprising the Fgl-2 gene as well as mammals and cell lines in which the expression of Fgl-2 has been suppressed.

Accordingly, in one aspect, the present invention provides a nucleic acid construct comprising a nucleic acid sequence comprising at least a portion of an Fgl-2 gene linked to a marker sequence.

In another aspect, the present invention provides an embryonic stem cell containing a nucleic add construct of the invention.

In a further aspect, thepresent invention provides a non-human animal and its progeny having decreased expression of the Fgl-2 gene.

In a further aspect, the present invention further provides a method of preparing a non-human animal with decreased expression of an Fgl-2 gene comprising inserting into the genome of the non-human animal a nucleic acid sequence comprising at least a portion of an Fgl-2 gene linked to a marker sequence.

The non-human animals of the present invention are useful in studying Fgl-2 and diseases wherein Fgl-2 is implicated including viral hepatitis, graft rejection, fetal loss syndrome, inflammatory bowel disease, lupus glomerulonephritis, acute respiratory disease syndrome, Whipple's disease and cancer. The non-human animals are also useful in identifying therapeutic agents that may be useful in treating these conditions.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

As hereinbefore mentioned, the present inventors have prepared nucleic acid constructs comprising the Fgl-2 gene as well as mammals and cell lines in which the expression of Fgl-2 has been suppressed.

A. Nucleic Acid Constructs

In order to prepare the knockout animal, the inventors first constructed nucleic acid constructs containing the Fgl-2 gene. The nucleic acid constructs were designed to decrease or suppress expression of Fgl-2 in a cell. The general features of the nucleic acid construct are that it contains a nucleic acid sequence from one or more regions of the Fgl-2 gene and a marker sequence that can be used to detect the presence of the construct in a cell.

Accordingly, in one aspect, the present invention provides a nucleic acid construct comprising a nucleic acid sequence comprising at least a portion of an Fgl-2 gene linked to a marker sequence.

The nucleic acid sequence comprising at least a portion of an Fgl-2 gene will include a sufficient complimentary sequence from the Fgl-2 gene for hybridization with the native gene when the nucleic acid construct is introduced into the genomic DNA of a cell. In one embodiment, the nucleic acid sequence comprises the entire Fgl-2 gene. The sequence of the Fgl-2 gene is provided in applicant's co-pending application Ser. No. 09/442,143. Preferably, one of the exons of the Fgl-2 gene is disrupted by a marker.

The marker can be any marker that can be used to detect the presence of the nucleic acid construct in a cell. A marker sequence may also be used to disrupt the expression of the Fgl-2 gene. The term "a marker sequence" as used herein means at least one marker sequence and includes several markers. Preferred marker genes are antibiotic resistance genes such as the neomycin resistance gene (neo), the reporter lacZ gene and the herpes simplex virus thymidine kinase gene (HSV-tk). The marker gene will preferably have a 3-UTR sequence attached to the 3' end of the gene which serves to stabilize the marker gene.

Figure 1A:
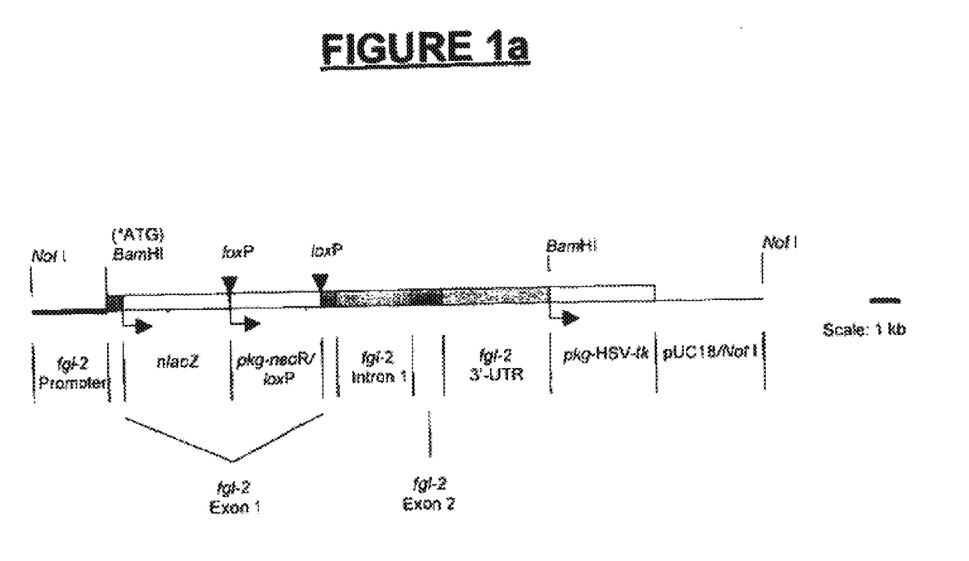
FIGS. 1a and b are schematic diagrams of the Fgl-2 vector.

Accordingly, in a preferred embodiment, the present invention provides a nucleic acid construct comprising (a) a nucleic acid sequence comprising an Fgl-2 gene or portion thereof; (b) a lacZ gene; (c) a neo-R gene; and (d) an HSV-tk gene. Preferably, the nucleic acid construct is as depicted in FIG. 1a.

In order to prepare the nucleic acid construct, the genomic DNA sequence containing the Fgl-2 gene is digested with restriction enzymes and the marker gene(s) is (are) ligated into the genomic DNA sequence using methods known in the art or as described in the Examples of the present application.

The nucleic acid construct containing the Fgl-2 gene and the marker can be inserted directly into embryonic stem cells or it may be placed into a suitable vector for amplification prior to insertion. Suitable vectors include a pUC18/NotI, Bluescript II, or pGEM7.

B. Transfection of Embryonic Stem Cells

The above nucleic acid constructs or vectors containing the construct can be used to transfect cells such as embryonic stem cells.

Accordingly, in another aspect, the present invention provides a cell, preferably an embryonic stem cell, containing a nucleic acid construct of the invention.

Embryonic stem cells are useful as they can integrate into and become part of the germline of the developing embryo so as to create germline transmission of the nucleic acid construct or vector carrying the Fgl-2 gene. Any embryonic stem cell that can integrate into the developing embryo may be used in the present invention. The embryonic stem cell is generally of the same species as the knockout to be prepared i.e., to make a knockout mice, mouse embryonic stem cells are used. In one embodiment, the embryonic stem cell are isolated from mouse blastocysts, in particular from the 129/SvJ strain. The cells can be cultured prior to transfection with the nucleic acid construct or vector using methods well known in the art including the methods taught by Robinson in Teratocarcinomas and Embryonic Stem Cells: A Practical Approach, E. J. Robinson editor, IRL Press, Washington, D.C., 1987.

The vector can be inserted into the cells using techniques known in the art including electroporation, microinjection and calcium phosphate treatment. Preferably, the vector is inserted using electroporation. Prior to insertion, the vector is first linearized using a suitable restriction enzyme that cuts within the vector sequence and not within the nucleic acid sequence containing the Fgl-2 gene and the marker. After insertion into the cells the nucleic acid construct integrates with the genomic DNA of the cell in order to prevent or inhibit transcription of the native Fgl-2 gene. Preferably, the insertion occurs by homologous recombination wherein regions of the Fgl-2 gene in the nucleic acid construct hybridize to the homologous Fgl-2 sequences in the cell and recombine to incorporate the construct into the endogenous Fgl-2 sequence.

After transfection, the cells are cultured under conditions to detect transfected cells. For example, when the marker gene comprises an antibiotic resistance marker, the cells are cultured in that antibiotic. In particular, when the neo-R gene is present, the cells can be cultured in the neomycin drug analog G418. The cells containing the vector survive while the non-transfected cells die. The DNA of the surviving cells can be analyzed using Southern Blot technology and/or the Polymerase Chain Reaction (PCR) as described in the Examples, in order to identify the cells with the proper integration of the construct.

C. Preparing Knockout Animals

The above described embryonic stem cells containing a nucleic acid construct or vector of the invention can be used to prepare a knockout non-human animal including mice, hamsters, rats and rabbits. Preferably the animal is a mouse. In particular, the embryonic stem cells are inserted to an early embryo for example using microinjection. For microinjection, approximately 10–20 embryonic stem cells are collected into a micropipette and injected into 3–5 day old blastocysts, preferably 3½ day old blastocysts, recovered from female mice. The injected blastocysts are re-implanted into a foster mother. When the pups are born, typically 20–21 days later, they are screened for the presence of the nucleic acid construct of the invention. For example, the tail tissue of the pups may be screened using Southern blots and/or PCR as described in the Examples. The heterozygotes are identified and can then be crossed with each other to generate homozygous knockout animals.

Accordingly, the present invention provides a non-human animal and its progeny having a nucleic acid construct of the invention inserted into its genome wherein the animal has decreased expression of the Fgl-2 gene.

The term "decreased express of the Fgl-2 gene" means that the expression of the Fgl-2 gene is decreased or suppressed as compared to an animal that does not contain a nucleic acid construct of the invention. The expression of the Fgl-2 protein may be completely or partially suppressed. Preferably, the Fgl-2 protein is completely suppressed, i.e., not expressed when measured by Southern blotting.

The present invention further provides a method of preparing a non-human animal with decreased expression of an Fgl-2 gene comprising inserting into the genome of the animal a nucleic acid construct comprising nucleic acid sequence from an Fgl-2 gene or a portion thereof linked to a marker sequence.

In a preferred embodiment, the method of preparing the non-human animal with decreased expression of an Fgl-2 gene comprises: (a) obtaining a nucleic acid sequence containing an Fgl-2 gene or portion thereof; (b) preparing a nucleic acid construct comprising the nucleic acid sequence containing the Fgl-2 gene and a marker gene, wherein said marker gene is inserted into an exon of the Fgl-2 gene; (c) inserting the nucleic acid construct into an embryonic stem cell: (d) selecting a cell that has integrated the nucleic construct into its genome; (e) injecting said cell into a blastocyst to form a chimeric blastocyst; (f) implanting said chimeric blastocyst into a pseudopregnant mother wherein said mother gives birth to a chimeric animal containing the chimeric construct in its germline; (g) breeding said chimeric animal to generate heterozygous animal that is heterozygous for the nucleic acid construct; and (h) mating together a male and female animal each heterozygous for the nucleic acid construct and selecting progeny that are homozygous for the nucleic acid construct.

In a preferred embodiment, the non-human animals of the invention are mice.

D. Use of the Knockout Animal

The knockout animals of the present invention are useful in studying Fgl-2 and diseases wherein Fgl-2 is implicated including viral hepatitis, graft rejection, fetal loss syndrome, inflammatory bowel disease, lupus glomerulonephritis, acute respiratory disease syndrome, Whipple's disease and cancer. The animals are also useful in testing therapeutic agents useful in treating these conditions.

As an example, an Fgl-2 a knockout animal of the invention can be used to screen an agent for therapeutic utility by administering the test agent to the animal at various doses and assaying the effects on the animal. In addition, the Fgl-2 knockout animals can be used to study the effect of decreased expression of Fgl-2 on these conditions. For example, an Fgl-2 knockout mouse may be infected with murine hepatitis virus (MHV) as described in Example 4 wherein it is demonstrated that the knockout mice survive longer than the wild type. As a result, this example demonstrates that Fgl-2 is involved in the pathogenesis of MHV.

The following non-limiting examples are illustrative of the present invention:

EXAMPLES

Example 1

I. Construction of Targeting Vector

Figure 1B:
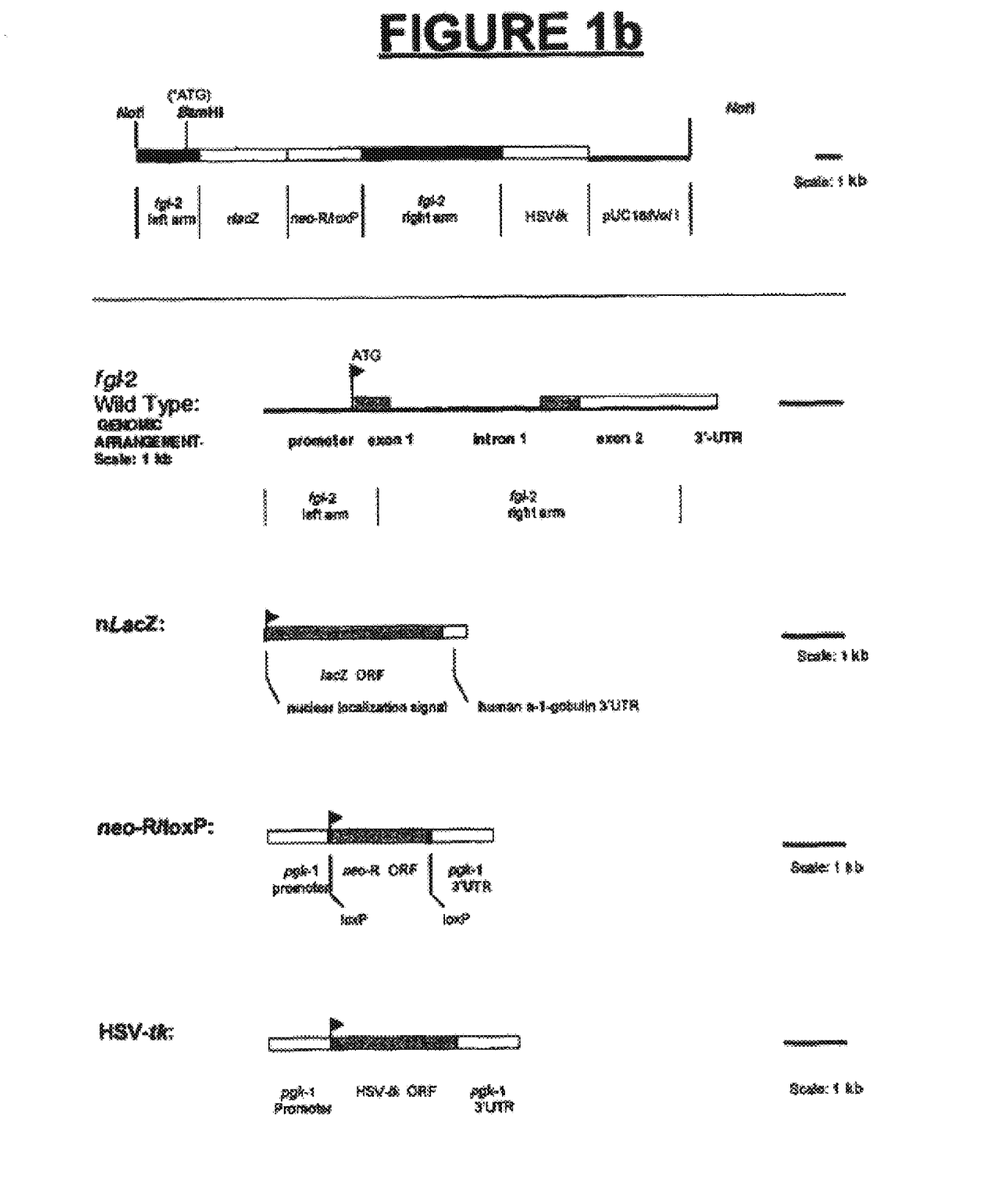

Using the Fgl-2 containing male mouse 129/SvJ genomic DNA, which was originally cloned in a P1 vector, a state-of-the-art replacement targeting vector was constructed for homologous recombination in embryonic stem cells. It consists of the 5'-promoter and the entire Fgl-2 gene, where its first exon was disrupted by a reporter gene (lacZ) followed by a dominant positive selectable marker (neo-R) that has been flanked by loxP sequences as shown in FIGS. 1a and b. The intact 5'-promoter region is for the regulatory studies of Fgl-2 in an authentic in vivo environment. The disruption of the gene in the first exon caused amino acid codon frame shifted and allowed the knockout of gene functions to take place. To make it more versatile, the disruption was done by cloning in the prokaryotic lacZ reporter gene to create a read out system for the Fgl-2 promoter. The tropic expression of Fgl-2 could therefore be studied in different tissues of the knockout mice in the presence of regulatory and stimulatory factors and reagents such as cytokines, immune-suppressors or repressors, and pathogens (e.g. viruses) etc. The importance of this gene during the embryonic development can be studied also by the detection of the lacZ product, beta-galactosidase in the embryonic tissues. It would be particularly crucial if the homozygous (−/−) knockout mice are phenotypically lethal, either during the embryonic development or after birth. The presence of lacZ product in different tissues at different stages would indicate the pivotal role of the Fgl-2. For event better visualization, the sequence of the nuclear localization signal was also cloned in just 5' to the lacZ, directing the expressed lacZ product into the nuclei of the cells for more intensified staining. To ensure stability, a human alpha-1-globulin gene derived 3'-UTR was cloned in at the end of lacZ.

The neomycin resistant gene (neo-R) was inserted right next to the lacZ and is for the enhancement of selecting positively targeted embryonic stem cells clones in the presence of neomycine analog G-418. The addition of cyclic recombinase sensitive loxP sequences that flanked the neo-R, is for the easy removal of the neo-R should the re-construction of another vector be necessary. Further manipulation to make other new targeting vectors is also possible by using the pre-cloned loxP sites in the future. A dominant negative selectable marker, herpes simplex virus thymidine kinase gene (HSV-tk), was also cloned in at the 3'-end of the targeting vector. Its function was to enhance clone selection by eliminating the possible gene insertion events instead of the expected gene replacement by homologous recombination in gene targeting in the presence of gancyclovir. Both the positive and the negative marker genes were purposely modified to ensure gene expression, using the strong PGK-1 (phosphoglycerate kinase-1) promoter for protein production and the PGK-1 3'-UTR for stability. The original translation initiation codon ATG of the Fgl-2 was mutated also to eliminate the potential dominant-negative effect, which might arise due to the possible partial-expression of the first undisrupted part of exon 1 in the +/− heterozygous phenotype. It was purposely mutated in a way to create an additional restriction enzyme site, Bam H1, for future screening use.

Example 2

Selection of Targeted Embryonic Stem (ES) Cell Clones

Principle

In order to incorporate the mutated Fgl-2 genomic DNA (in targeting vector) into the ES cells for the targeting homologous recombination to occur, the NotI-restriction enzyme linearized targeting vector was electroporated into the healthy ES cells, which was isolated from mouse 129/SvJ blastocysts. The transfected ES cells were distributed to cultures coated with feeder cells (129/SvJ embryonic fibroblasts, MEF cells) for 1 day before the neomycin analog drug G418 was added to the complete culture medium. Those ES cells that were targeted and thus carried the mutated Fgl-2 alleles could survive in the G418 drug because of the presence of a built-in neomycin resistant gene (neo-R) in the mutated vector. The non-targeted wild type (WT) ES cells, on the other hand, died because of the lack of the neo-R and could not survive in the G418 environment.

Figure 2:
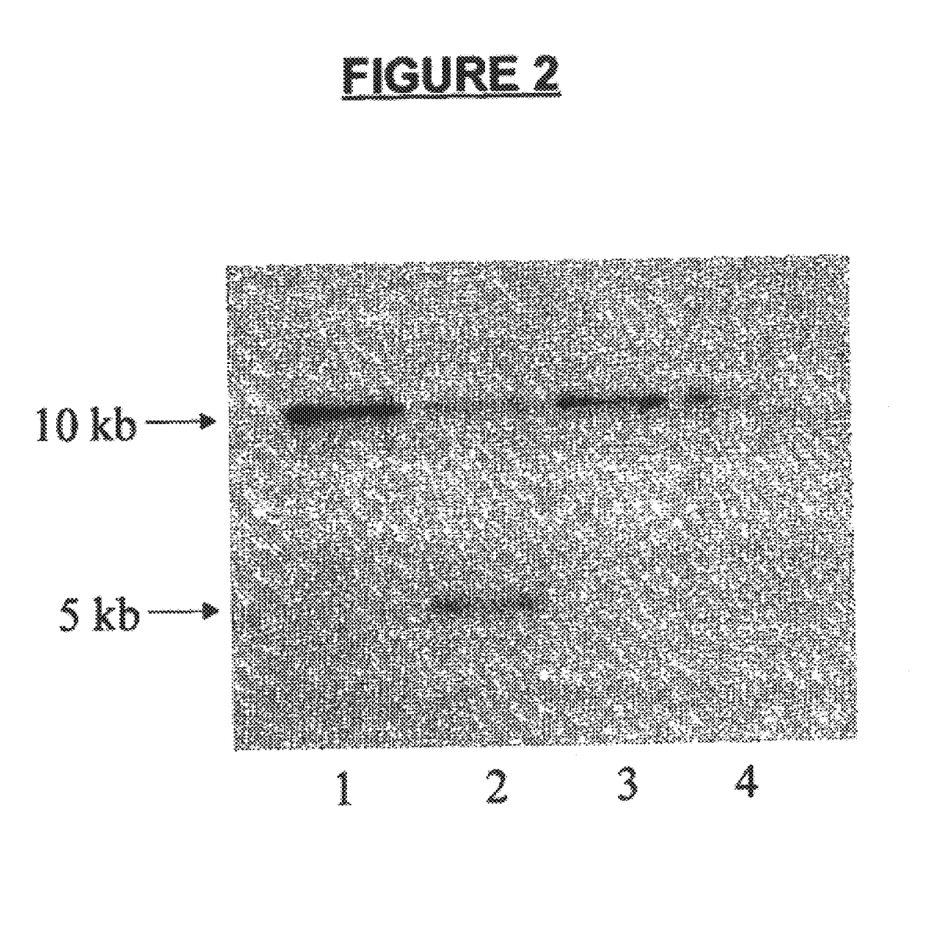
FIG. 2 is a genomic Southern blot of Fgl-2 knockout ES cells.

The surviving targeted ES cell clones were microscopically picked and cultured separately. The individually grown ES cell clones were harvested and isolated for genomic DNAs. DNAs were analysed on their restriction fragment patterns using genomic Southern blot technology to select for the replacement targeting through homologous recombination (targeted knockout) and to differentiate it from the unwanted gene insertion events. A radioactive P-32 labelled XbaI-EcoRV restriction fragments (1.5 kb in size) was excised from the 5' flanking region of the Fgl-2 gene as a probe. It was located just 5' outside the targeting vector sequences and was not included in the targeting vector. The restriction fragment analysis by BamHI digestion on the targeted genomic DNAs showed a different pattern in fragment size as compared to the WTs. The mutated targeting vector, in which the translation starting codon site ATG was mutated to form a BamHI recognition site, was subject to BamHI digestion. Together with another BamHI cutting at about 5 kb upstream of the mutated ATG site, a 5 kb BamHI fragment which was recognized and hybridized by the probe. On the other hand, there was no mutation to the ATG site of the WT and resulted in no cutting by the BamII at that ATG location. The next nearest BamHI site was about 5 kb downstream from the ATG site. The digestion by the BamHI, therefore, showed a probe recognized-10 kb fragment instead. The fact that there was a specific 5 kb BamHI fragment in the mutated (knockout) allele as compared to the 10 kb fragment in the wild type allele formed the basic principle of our screening method by genomic Southern blot techniques. Because the targeting vector did not encode the probe sequences, any insertion event therefore could not show the described patterns. The result of the screening selection of our knockout-positive ES cell clone is shown in FIG. 2. FIG. 2 shows 4 representative samples. Lanes 1, 3 and 4 non-targeted WT (+/+), showing only one 10 kb band. Lane 2—heterozygous KO (+/−) mutant, showing both of the 10 kb and 5 kb bands. Genomic DNA from G418 surviving clones showed only a 10 kb BamHI fragment band were the ones survived because of the insertion of the targeting vector containing the neo-R somewhere in the genome. Those were not resulted from replacement by homologous recombination, and thus could not create the 5 kb BamHI fragment that could be probed by the designed probe. They were still Fgl-2 +/+ WTs and were not used in the further development of the knockouts. The +/− heterozygous mutants showed both the 10 kb and 5 kb bands, indicating the presence of a replacement homologous recombination in one of the alleles. They were used to create the mouse Fgl-2 knockout lines. The −/− homozygous mutants, which rarely produced in the ES cell targeting due to the extremely low possibility for recombinations to occur in both alleles at the same time, was not detected in the selection.

Methodology

I. 129 Sv/J Mouse Embryonic Stem (ES) Cells and Embryonic Fibroblast (MEF) Feeder Cells. Cells were isolated from mouse 129Sv/J blastocytes and supplied at passage 2 by Genome Systems (now Incyte, St. Louise, Mo., U.S.A.). Culture conditions were followed as described by Genome System. The addition of leukemia inhibitory factor (LIF) was to keep the ES cells at the pluripotent stage and MEF feeder cells was for the proper growth.

II. Targeting DNA and Electroporation. The targeting vector DNA was linearized by complete digestion of restriction enzyme NotI. The linearized DNA was purified by TAE agarose gel electrophoresis and recovered by Gene Clean reagents and precipitation after excising from the gel. The linearized targeting vector DNA was then transfected the ES cells at passage 3 by electroporation. It was followed by distribution to the 24-well tissue culture plates containing mitotic-inactivated MEF cells, (by a 2-hour incubation with mitomycin C followed by thorough raising) for 24 hours for establishment.

III. Selection of Targeted ES cells. The culture medium was exchanged by the selection medium, which contained G418 for selecting the neomycin resistant alleles and leukemia inhibitory factor for maintaining ES cells in pluripotent stage, every day for the next five days to select the targeted ES cells. The G418 surviving clones were microscopically picked on the sixth day after electroporation. The selected clones were trypsinized and transferred to MEF feeder cell-coated 24 well plates for culture. Two days later the plates were trypsinized and split into duplicates. The clones would grow for two more days. Then each one of the duplicate plates were DNA-extracted for genotyping while the other duplicates were kept frozen and saved for further expansion once the genotypes were known.

IV. ES Cell Screening (Genotyping). Genomic DNA was extracted as described by Genome System and elsewhere for genomic Southern blot analyses. Extracted DNA from different clones were subject to TAE gel electrophoresis, immobilization to nylon membrane (Amersham) by downward transfer overnight in 20 SSC buffer and UV-crosslinking, prehybridization at 42° C. with 50% formamide (in Denhardt hybridization solution and denatured salmon sperm DNA as blocker) for 5 hours, and hybridization in the same solution with the heat-denatured alfa P-32 labelled probe of XbaI-EcoRV DNA fragment (1 million cpm/ml). The 1.5 kb probe was labelled for 4 hours by random priming at room temperature by Gibco (Grand Island, N.Y.) reagent kit followed by purification with Pharmacia Nick Column chromatography. Hybridization was done at 42° C. for 24 hours. Visualization of result was achieved by either using the phosphor imaging technique (Storm system) or by standard x-ray film exposure. The clones showed the band pattern of having both the 10 and 5 kb site were Fgl-2 targeted +/− heterozygous knockouts. They were selected for blastocyst injection after re-growing from the frozen master plates and expansion.

Example 3

Generation of Mouse Fgl-2 Knockout Line

Generation of Chimeras

Figure 3:
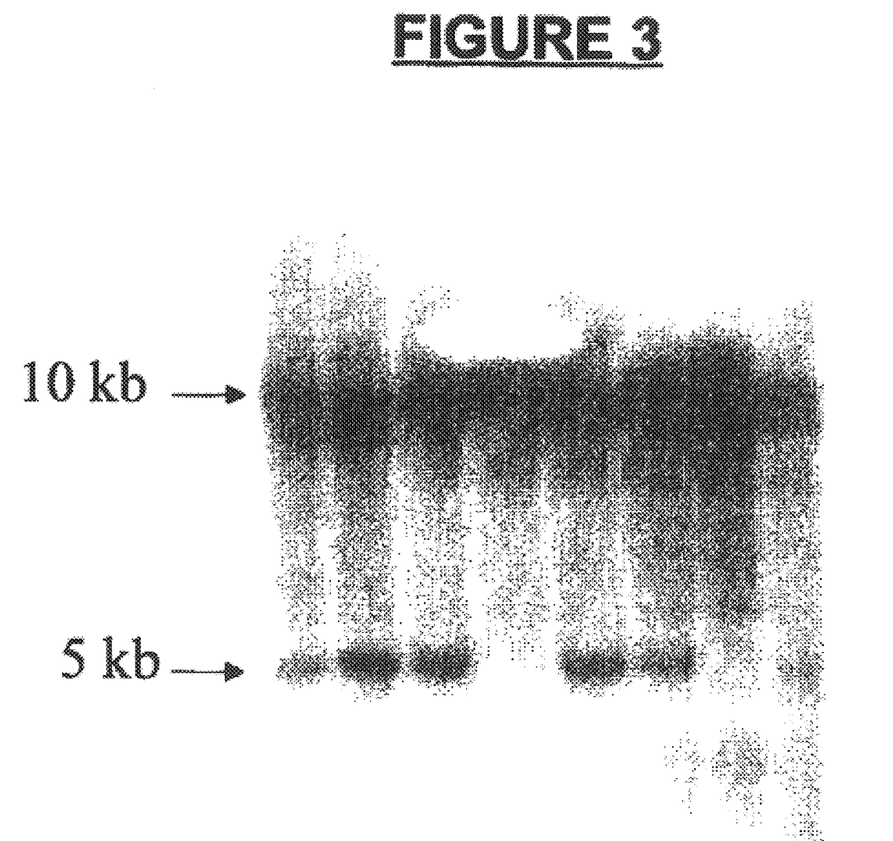
FIG. 3 is a genomic Southern blot of Fgl-2 knockout F1 mice.

The 2-day old Fgl-2 targeted ES cells (+/−) were dissociated well by trypsinization. Ten to twelve cells were injected into each 3½ day-old blastocyst recovered from female C57Black/6 (B6) mice by micromanipulator (all the procedures were carried out by the trained staff of the Ontario Cancer Institute, University Health Network of University of Toronto). Injected blastocysts were re-implanted (transferred) to female ICR mice as foster mothers for the embryos. Approximately 15 to 20 blastocysts were implanted to each foster mother. The foster mothers were returned to sterile cages in the colony after surgery. Litters were born 18–19 days later. Among the newly born pups there were 9 male and 2 female chimeras with different degree of agouti colour furs. To determine whether these chimeras had targeted Fgl-2 ES cells developed into germ cells, the chimeras were mated with B6 mice to generate the F1 mice. The F1's were screened and genotyped (FIG. 3) for germline transmission. FIG. 3 shows 4 representative samples. Lanes 1, 3 and 4 non-targeted WT (+/+), showing only one 10 kb band. Lane 2—heterozygous KO (+/−) mutant, showing both of the 10 kb and 5 kb bands. Out of 9 male chimeras, 5 of them were Fgl-2 knockout heterozygous, indicating the production of Fgl-2 +/− germ cells. None of the 2 female chimeras had the germline transmission. The F1 founders were (1) cross-mated to produce the homozygous (−/−) and the (+/−) heterozygous knockout mice in Mendelian fashion, and (2) kept on mating with B6s to expand the heterozygous colonies and to achieve creating a mouse Fgl-2 knockout homozygous mutant on C57Black/6.

Screening and Genotyping

Tail DNAs of the mice were used for the screening. Generally the tails were cut at about 1 cm from the tip at the age of 3 weeks when they were just weaned. Genomic DNAs were extracted using proteinase K digestion and alcohol precipitation method well described elsewhere. Three methods were used to assure the genotyping was accurate.

Figure 4:
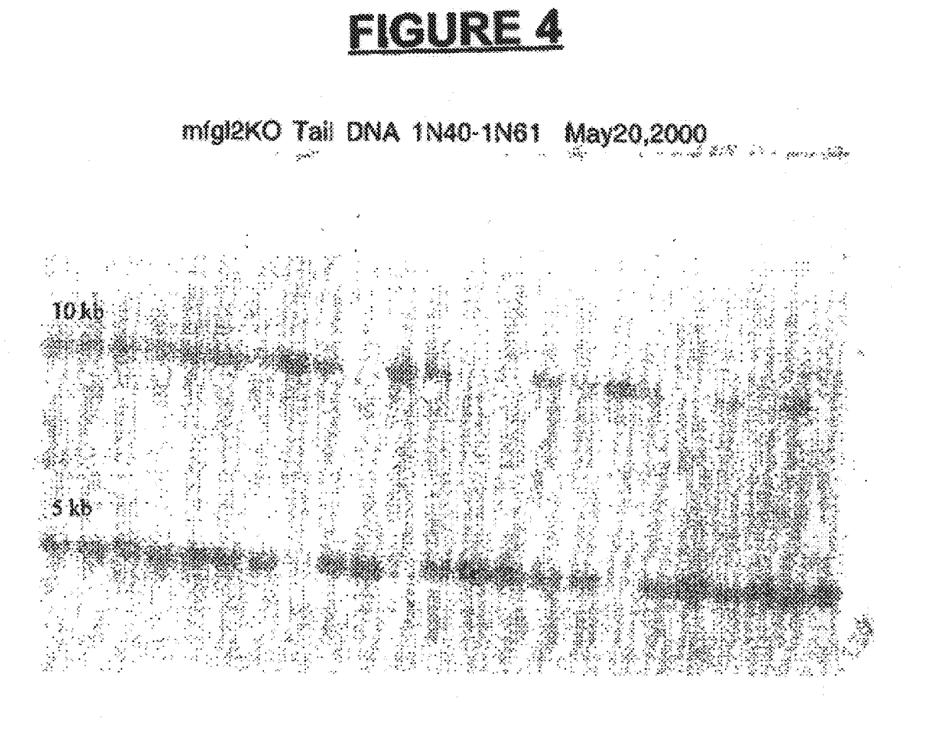
FIG. 4 is a genomic Southern blot of Fgl-2 knockout F2 mice.

(1) Genomic Southern Blot. As described in the ES cell screening with some modification in the hybridization and labelling. Labelling of probes was carried out with Read-To-Go DNA labelling beads (dCTP) (Amersham Pharmacia Biotech, Piscataway, N.J., U.S.A.) for 30 minutes. The modification increased the efficiency about 2 to 4 folds. The prehybridization and hybridization were also changed for a better result. A single pre-mixed prehybridization and hybridization solution ULTRAhyb from Ambion (Austin, Tex.) was used. The reactions, including washings, were carried out at 50° C. The changes increased the signals 20 to 50 folds. FIG. 3 shows a Southern Blot of the genomic screening of Fgl-2 knockout F1 mice and FIG. 4 shows a Southern Blot of the genomic screening of Fgl-2 knockout F2 mice.

Figure 5:
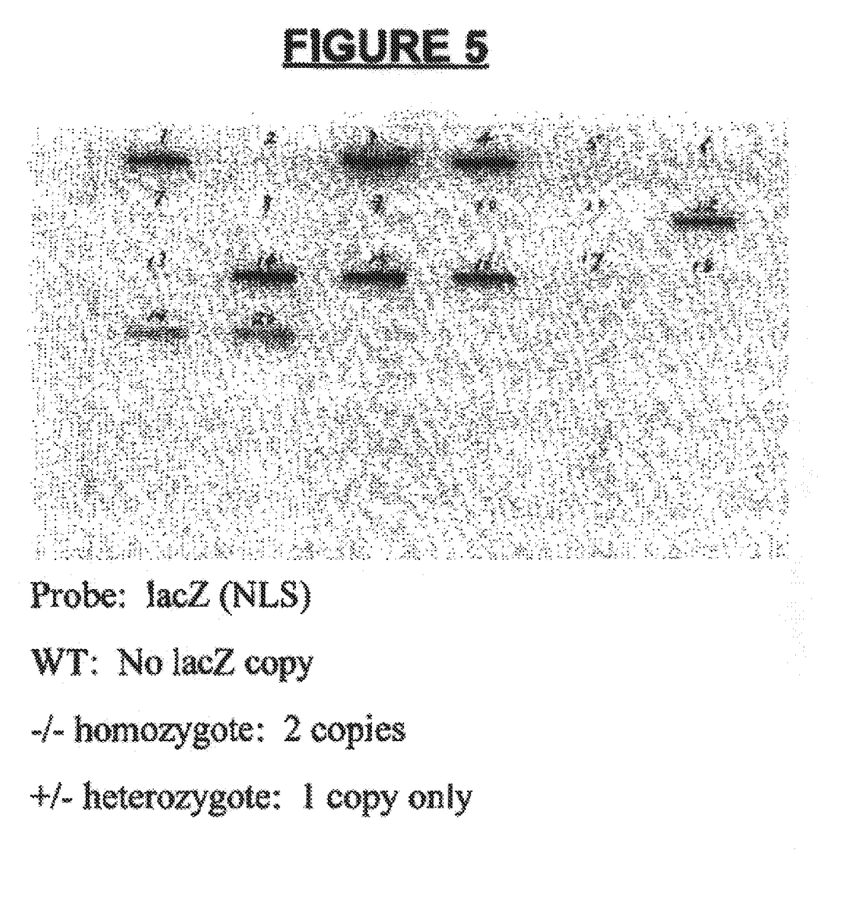
FIG. 5 is a blot showing the genotyping of Fgl-2 knockout mice by lacZ copy screening.

(2) LacZ gene probing for copy number of incorporation of the Fgl-2 gene. The lacZ gene, which was constructed in the targeting vector, was used to differentiate the wild type sequences (lacking lacZ; +/+) from the targeted (presence; +/− and −/−). Also the presence of only one targeted copy DNA (one of the two alleles; +/− heterozygote) mathematically showed half of the amount of those with two targeted copies (both of the alleles; −/− homozygote). Ten micrograms of tail DNAs from individual mouse were loaded into slots of slot blotter and were immobilized onto nitrocellulose membrane by suction. Control standards of plasmid DNA containing different known copies of lacZ gene (courtesy of Dr. Schult from Department of Medical Genetics at the University of Toronto) was also loaded on the same blot with equivalent molarity. After the DNAs were cross-linked to the membrane by UV-activation, the blots were then probed with a P-32 labelled 1.1 kb BamHI-SacI restriction fragment which could be found only in the lacZ gene. The results of the probing were visualized by phosphor imaging technique and the intensity of the DNA slots images were compared to the control standards to determine the number of copies of lacZ in the genome. Wild type non-targeted (+/+; background only), heterozygous (+/−, half of −/−), and the knockout homozygous (−/−, double of +/−) genotypes were clearly distinguishable from the blots. Some of the results are shown in FIG. 5.

Figure 6:
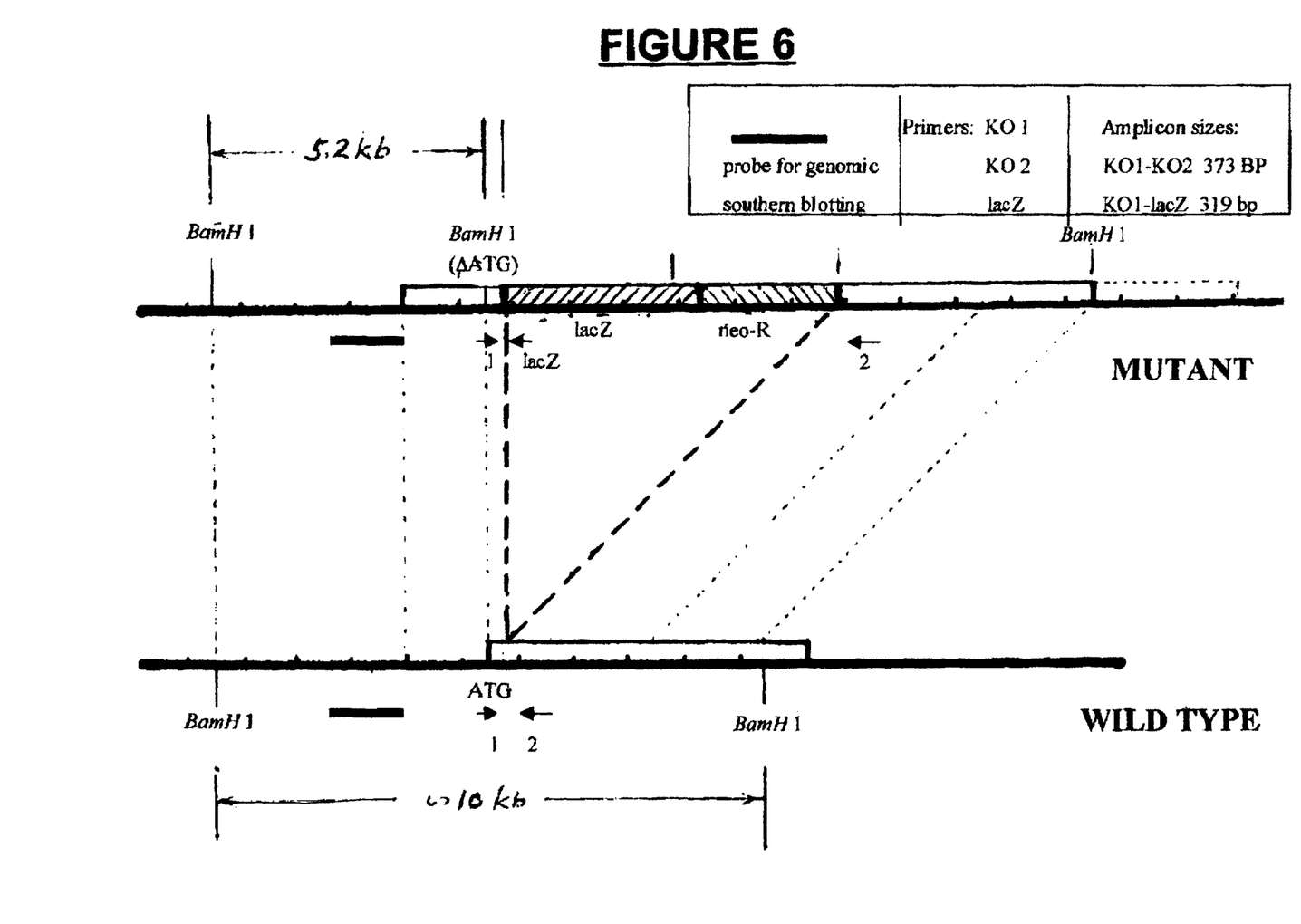
FIG. 6 is a schematic showing the probes and primers used for genotyping of Fgl-2 knockout mice.
Figure 7:
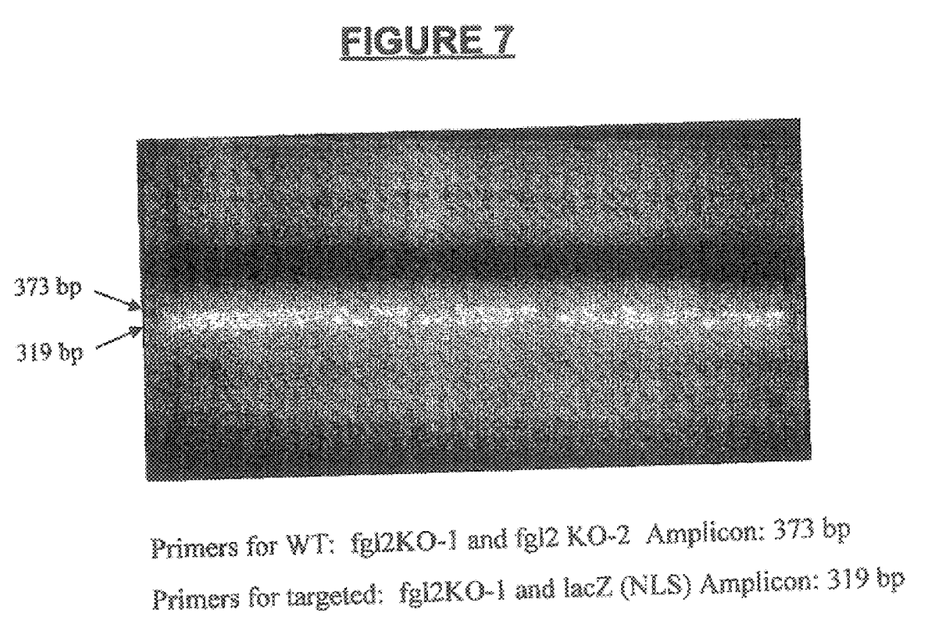
FIG. 7 is a blot showing the genotyping of Fgl-2 knockout mice by multiplex PCR.

(3) Multiplex Polymerase Chain Reaction (Multiplex PCR). PCR methods were also used for genotyping the tail DNAs. The first set of primers was to show the presence of WT genotype. Primers mFgl-2-KO1 (sense primer) and mFgl-2-KO2 (anti-sense primer) were designed to amplify the sequences across the junction of insertion where the additional lacZ and neo-R genes interrupted the first exon of Fgl-2 (FIG. 6). The amplicon size was 373 bp for the wild type sequences. Since there were additional lacZ and neo-R gene sequences of about 6 kb placed in between the two primers in the targeted DNAs, it was obvious that the sequences were too long for the PCR method to amplify. Therefore there was no PCR product for the knockout sequences. Another sets of primers were also designed to show the presence of knockout sequences instead. The Fgl-2-KO1 sense primer was still used. The antisense primer, lacZ-AS in NLS, was chosen from the sequences of the nuclear localization signal of the lacZ gene, which was just at the junction of the site of Fgl-2 interruption. The amplicon size on the targeted sequences was 318 bp. Whenever there were targeted sequences in the DNA sample, the PCR product of 319 bp would show. Because there was no nuclear localization signal sequences in the wild type, the antisense primers could not anneal to any complementary sequences thus could not produce any amplicon. The designed multiplex PCR, of which both the primer sets required the same conditions to amplify, resulted in the different patters in the analyses using gel electrophoresis. Conclusively, wild types showed a single amplicon band of 373 bp, the homozygous knockouts showed a single band of 319 bp, and the heterozygotes showed both of bands of 373 and 319 bp. Some of the results are shown in FIG. 7. The primer sequences are as follows.

(1) mfg12-KO1: 5'-TGCTCAAAGAAGTGCGGACCCT-3' (22-mer; sense) (SEQ ID NO:1)

(2) mfg12-KO2 : 5'-CACCTACCCGGCTGTGACTGC-3' (21-mer; antisense) (SEQ ID NO:2)

(3) lacZ-AS in NLS: 5'-CCCATGCTCCCCACTTTGC-3' (19-mer; antisense) (SEQ ID NO:3)

Example 4

In vitro and in vivo Experiment with MHV-3

I. Evidence of Null fgl-2 Knockout Mutant

To further prove that there was a completed Fgl-2 knockout and there is no pseudo-gene in the genome of the null knockout mutant mice (fgl2 −/−), reversed transcription-polymerase chain reactions (RT-PCR) were performed. Fgl2 wild type macrophages, which have showed activation of Fgl-2 gene in mouse hepatitis infections, were used as a specific cell target for the expression in vitro. Whereas the liver tissues were used in in vivo experiments because liver is the major targeted organ in hepatitis studies.

Figure 8:
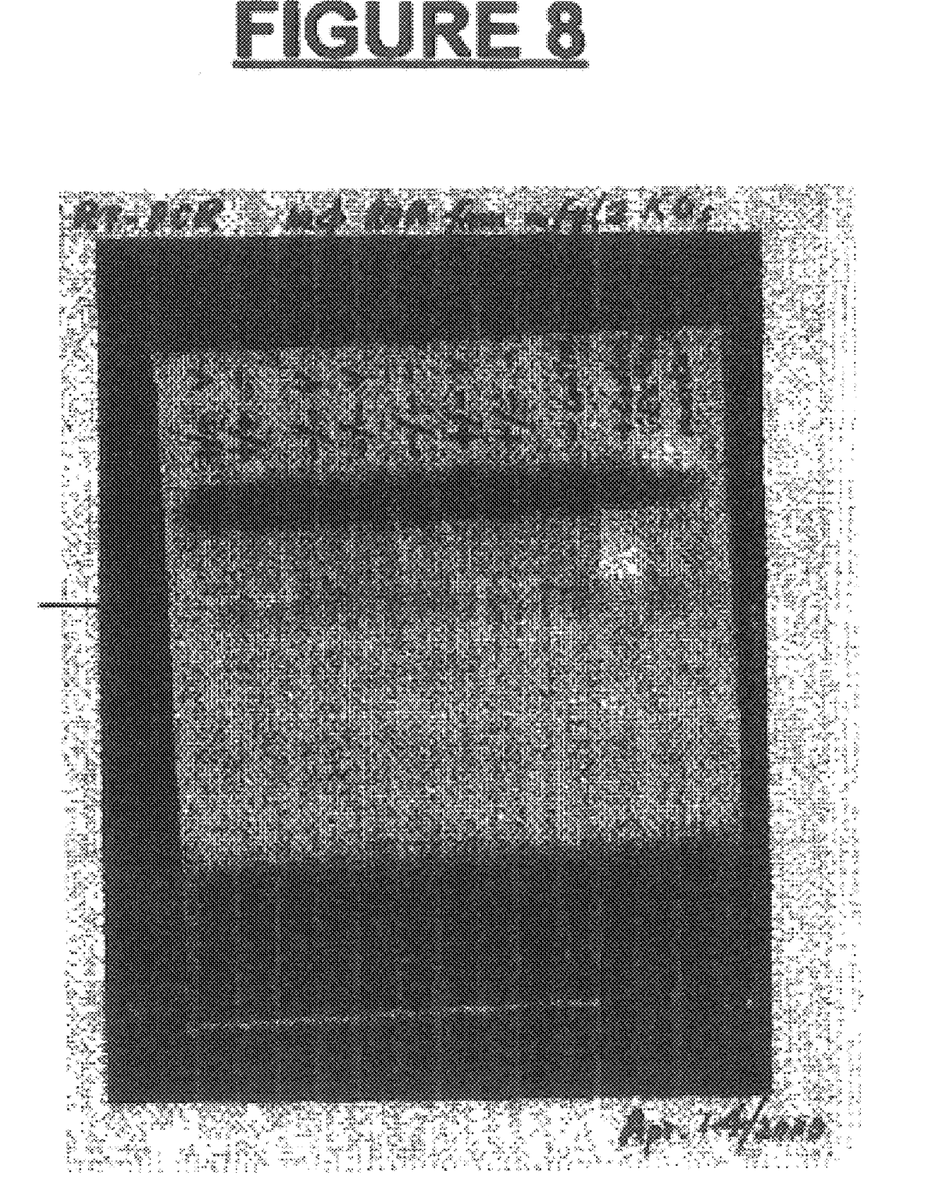
FIG. 8 is an agarose gel showing lack of detection of Fgl-2 mRNA by RT-PCR in macrophages from Fgl-2 −/− mice.

Peritoneal macrophages from mice of different knockout genotypes (−/−, +/−, and +/+ littermates) were harvested 4 days after injection (I.P.) of 2 ml of aged 3% Brewer's thioglycollate. Washed macrophages were infected by mouse hepatitis virus strain 3 (MHV-3) at the multiple of infection (M.O.I.) of one in completed RPMI1640 culture medium with 2% fetal bovine serum. Infection/stimulation was carried out for 8 hours before total RNA (ribonucleic acid) was extracted. The total RNA extractions were done following the protocol of the StrataPrep Total RNA Miniprep Kit (catalog #400711) from Stratagene in La Jolla, Calif., U.S.A. The total RNA extracted was used to synthesize the first strands of cDNA (complementary deoxyribonucleic acid), using reversed transcription protocol of SuperScript Preamplification System for First Strand cDNA Synthesis (Random hexamer method) from Life Technologies/Gibco BRL of Rockville, Md., U.S.A One tenth of the synthesized cDNAs were used to perform the PCR amplification by a set of Fgl-2 specific primers (sense primer: mfgl-2 KO1 and antisense primer: mfgl-2 KO4) where the sequences were franking the first exon/intron junction. PCR was carried out for 30 cycles at optimal conditions with taq polymerase. Any existed Fgl-2 wild type (non-targeted) allele would have no insertional sequences and therefore an amplicon of 430 bp could be seen after PCR and subsequent agarose gel electrophoresis of the PCR products. As for the targeted mutants, because of the presence of the additional 6 kb of nLacZ and neo-R loxP gene sequences in between the primers, no amplification product could be shown as the present technology cannot amplify such a large piece of sequence. FIG. 8 shows that 430 bp bands of the PCR amplicon of +/+ knockout littermate (both alleles were wild type fgl2 +/+) infected with MHV-3 (V) and non-infected (−); −/− null homozygous mutant (both alleles were mutant fgl2 −/−) infected with MHV-3 (V) and non-infected (−); and +/− heterozygous knockout mutant (one allele wild type +/− and the other mutant −/−) infected with MHV-3 (V) and non-infected (−). Since there is small constitutive expression of fgl2 constantly in mice, the non-infected macrophages of +/+ littermate and +/− heterozygote showed the presence of wilt type fgl2 product as that of infected macrophages because they contained at least one wild type allele. The −/− homozygous mutant, regardless of the presence (V) of MHV-3 or not (−), showed no 430 bp band of PCR amplification, indicating that there was no intact non-targeted (wild type) fgl2 gene or a pseudo-gene in the genome. The fgl2 specific primers used for these experiments were the sense primer mfgl2-KO1 (5'-TGCTCAAAGAAGTGCGGACCCT-3') (SEQ ID NO:1) and the antisense primer mfgl2-KO4 (5'-GCCCCACTGCTTCTCCTTCCT-3') (SEQ ID NO:4).

Figure 9:
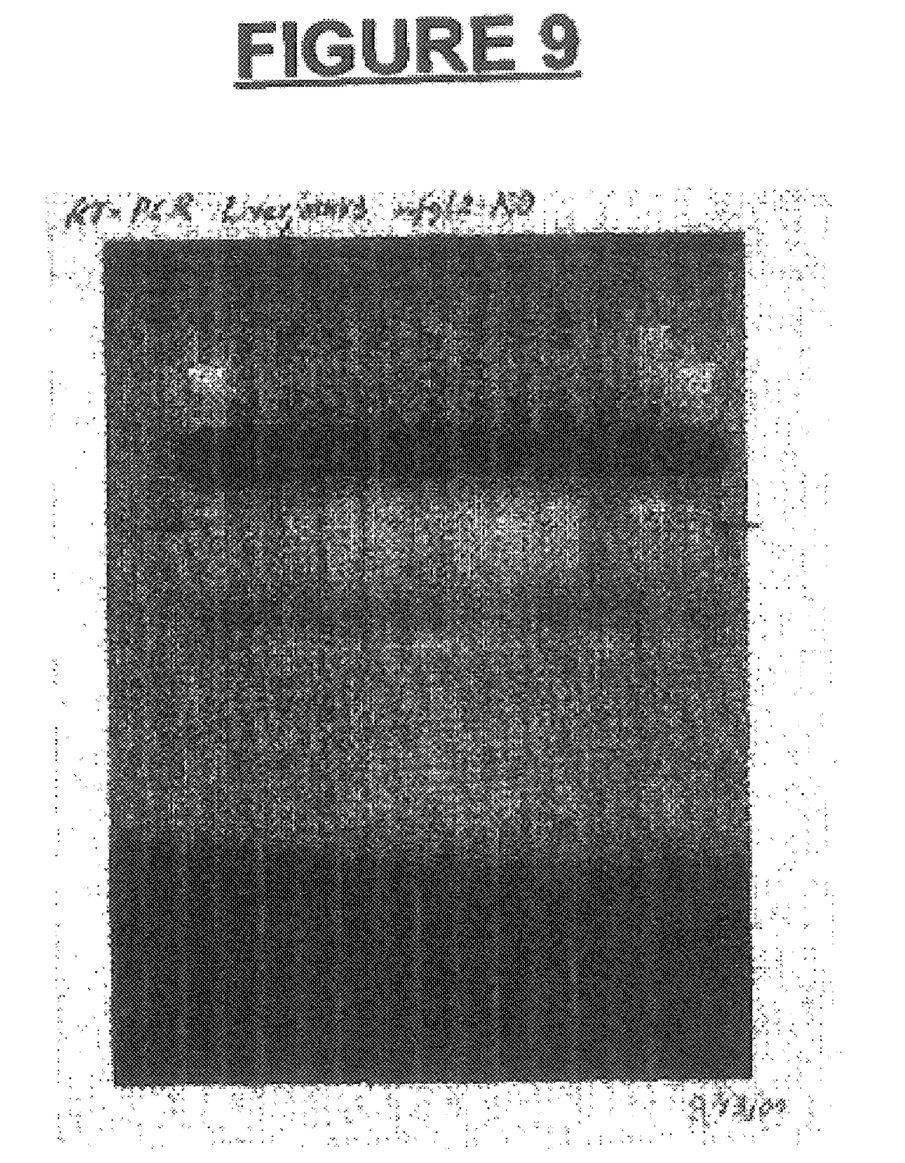
FIG. 9 is an agarose gel showing lack of detection of Fgl-2 mRNA in liver tissue from Fgl-2 −/− mice.

Similar principles applied to the in vivo liver tissue experiment. One thousand pfu (plaque forming units) of MHV-3 per mouse were injected (i.p.) to experimental mouse groups. Liver tissues were harvested at 16 hours post infected. Total RNA was extracted, followed by first strand cDNA synthesis and PCR amplification as described above. PCR products were resolved by gel electrophoresis. FIG. 9 shows that the −/− homozygous knockout mutant could not generate the wild type 430 bp amplicon (size shown by arrows); whereas the heterozygous +/− knockout and the +/+ littermates showed the 430 bp amplification product. The mouse strain C57Black/6 was also included for it is a MHV-3 susceptible strain in which the present mfgl2 knockout mouse line is being bred to.

II. In vivo Survival Experiment for Susceptibility.

In order to study the effects of targeted mutation of fgl2 gene on the susceptibility of mouse to MHV-3 induced fulminant hepatitis in vivo, groups of mice were challenged by the MHV-3 infection. One thousand (1000) p.f.u. of MHV-3 per mouse was injected i.p. into groups of 10 mice per experiment. These were the control groups of C57Black/6 (susceptible strain) and A/J (resistant strain), and the experimental groups of fgl2 homozygous (−/−) and heterozygous (+/−) mutants and wild type (+/+) littermates.

Figure 10:
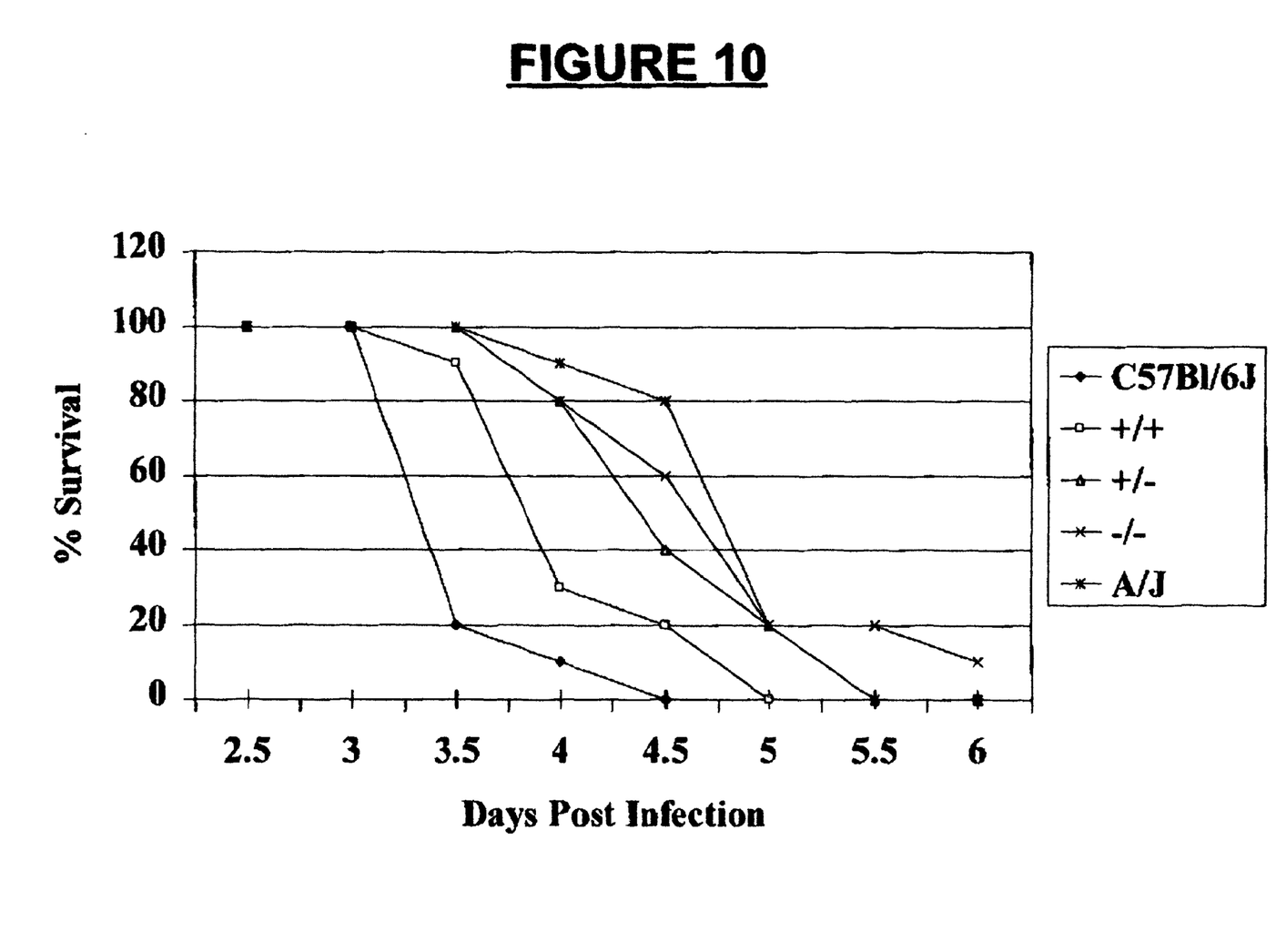
FIG. 10 is a graph showing effect of Fgl-2 −/− on course of MHV-3 induced fulminant viral hepatitis.

Daily progress of disease was monitored after injection. The results, shown in FIG. 10, demonstrate that the severity of spectrum of mortality had shifted. The highly susceptible C57Black/6 (fgl2 wild type) showed the usual early death caused by MHV-3 infection. However there is a pattern evolved in the delay of lethality or the extension of survival in the fgl2 knockout mice. This could be very significant in the studies of fulminant hepatitis pathogenesis.

III. In vivo Activation of MHV-3 Stimulation

One thousand (1000) p.f.u. of MHV-3 in 100 ul will be injected i.p. into 15 (if availability permits) mfg1-2 KO littermates (−/−) mice and other experimental groups (+/+ B6s, and +/+ and +/− KO littermates). Mock infection with PBS only will be done on similar groups as negative controls. Visual examination of infected groups will be carved out semi-daily for signs of infection. At different time points post infection (1, 2, 3, 4, 5, 7, 10, and 14 days p.i.) mice will be euthanatized and organs like livers, spleens, and intestines, etc. will be harvested as follows after thorough visual examination.

(A) A portion of the organs will be snap-frozen in liquid nitrogen for viral growth study in organs (viral titre);
(B) A portion of the organs will be embedded in OCT preservative and frozen in liquid nitrogen for immunostainings; and
(C) A portion of the organs will be fixed in buffered formaldehyde or para-formaldehyde for H & E histology studies and lacZ/beta-gal expression study, if necessary.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A nucleic acid construct comprising in the 5' to 3' direction a promoter; a nucleic acid sequence from an Fgl-2 gene or a portion thereof and a marker sequence, wherein the Fgl-2 gene is disrupted by the marker sequence.

2. A nucleic acid construct according to claim 1 wherein the marker sequence comprises a neo-R gene.

3. A nucleic acid construct according to claim 1 wherein the marker sequence comprises a lacZ gene.

4. A nucleic acid construct according to claim 1 wherein the marker sequence comprises an HSV-tk gene.

5. A nucleic acid construct according to claim 1 comprising:
   (a) a nucleic acid sequence comprising an Fgl-2 gene or portion thereof,
   (b) a lacZ gene;
   (c) a neo-R gene; and
   (d) an HSV-tk gene.

6. A nucleic acid construct according to claim 5 wherein the lacZ gene and the neo-R gene are inserted into the Fgl-2 gene.

7. A nucleic acid construct as illustrated in FIG. 1a.

8. A cell containing a nucleic acid construct according to claim 1.

9. A cell according to claim 8 which is a mouse embryonic stem cell.

10. A mouse having a nucleic acid construct according to claim 1 inserted into its genome wherein the mouse has decreased expression of the Fgl-2 gene and increased survival as compared to wild-type mice when infected with mouse hepatitis viral strain 3 (MHV-3).

11. A method of preparing a mouse with decreased expression of an Fgl-2 gene and increased survival as compared to wild-type mice when infected with mouse hepatitis viral strain 3 (MHV-3) comprising inserting into the genome of the mouse a nucleic acid construct according to claim 1.

12. A method of preparing a mouse with decreased expression of an Fgl-2 gene and increased survival as compared to wild-type mice when infected with mouse hepatitis viral strain 3 (MHV-3) according to claim 11 comprising:
   (a) obtaining a nucleic acid sequence containing an Fgl-2 gene or portion thereof;
   (b) preparing a nucleic acid construct comprising a nucleic acid sequence containing the Fgl-2 gene and a marker gene, wherein said marker gene is inserted into the Fgl 2 gene;
   (c) inserting the nucleic acid construct into an embryonic stem cell;
   (d) selecting a cell that has integrated the nucleic construct into its genome;
   (e) injecting said cell into a blastocyst to form a chimeric blastocyst;
   (f) implanting said chimeric blastocyst into a pseudopregnant murine mother wherein said mother gives birth to a chimeric animal containing the chimeric construct in its germline;
   (g) breeding said chimeric mouse to generate a heterozygous mouse that is heterozygous for the nucleic acid construct; and
   (h) mating together a male and female animal each heterozygous for the nucleic acid construct and selecting progeny that are homozygous for the nucleic acid construct and have decreased expression of an Fgl-2 gene and increased survival as compared to wild-type mice when infected with mouse hepatitis viral strain 3 (MHV-3).

* * * * *